(12) United States Patent
Antikainen et al.

(10) Patent No.: US 9,690,008 B2
(45) Date of Patent: Jun. 27, 2017

(54) ARRANGEMENT AND METHOD FOR ICING DETECTION

(75) Inventors: Petteri Antikainen, VTT (FI); Andrea Vignaroli, VTT (FI); Esa Peltola, VTT (FI)

(73) Assignee: Teknologian Tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 14/129,996

(22) PCT Filed: Jun. 15, 2012

(86) PCT No.: PCT/FI2012/050613
§ 371 (c)(1),
(2), (4) Date: Dec. 30, 2013

(87) PCT Pub. No.: WO2013/004893
PCT Pub. Date: Jan. 10, 2013

(65) Prior Publication Data
US 2014/0192356 A1    Jul. 10, 2014

(30) Foreign Application Priority Data

Jul. 1, 2011    (FI) ..................................... 20115701

(51) Int. Cl.
*G01W 1/02*    (2006.01)
*G01S 17/58*    (2006.01)
(Continued)

(52) U.S. Cl.
CPC ............ *G01W 1/02* (2013.01); *G01N 21/538* (2013.01); *G01S 17/58* (2013.01); *G01S 17/95* (2013.01);
(Continued)

(58) Field of Classification Search
CPC .......... G01W 1/02; G01S 17/95; G01S 7/003; G01S 13/95; G01S 17/023; G01S 17/003;
(Continued)

(56) References Cited

U.S. PATENT DOCUMENTS 5,214,484 A    5/1993    de Mollerat du Jeu
7,092,091 B2 *    8/2006    Itoh .................... G01N 21/9506
356/338

(Continued)

FOREIGN PATENT DOCUMENTS

CN    1684871    10/2005
CN    101792021    8/2010
(Continued)

OTHER PUBLICATIONS http://en.wikipedia.org/wiki/Lidar.*
(Continued)

*Primary Examiner* — Tarifur Chowdhury
*Assistant Examiner* — Mohamed K Amara
(74) *Attorney, Agent, or Firm* — Mark M. Friedman

(57) ABSTRACT

A method for detecting atmospheric icing potential comprises emitting, by a Doppler lidar (light detection and ranging) entity, electromagnetic radiation to the atmosphere and receiving radiation backscattered from the aerosol, such as a cloud, present in the atmosphere. From the received backscattered radiation, an indication of the icing potential at a number of distances, on the basis of the comparison and an indication of the temperature at the one or more distances, is determined.

18 Claims, 3 Drawing Sheets

(51) Int. Cl.
*G01S 17/95* (2006.01)
*G01W 1/04* (2006.01)
*G01N 21/53* (2006.01)
G01N 21/17 (2006.01)
G01N 21/47 (2006.01)

(52) U.S. Cl.
CPC ....... *G01W 1/04* (2013.01); *G01N 2021/1795* (2013.01); *G01N 2021/4709* (2013.01)

(58) Field of Classification Search
CPC ...... G01S 13/951; G01S 15/885; G01S 17/88; G01S 17/89; G01N 21/538; G01N 21/47; G01N 2021/4709; G01N 21/53; G01N 15/0205; G01N 2021/1795; G01N 2021/1793; G01N 21/65; G01P 5/26; G01P 5/01
USPC ........ 356/342, 338, 336, 337; 250/575, 236; 702/3
See application file for complete search history.

(56) References Cited

U.S. PATENT DOCUMENTS

| | | | |
|---|---|---|---|
| 7,580,127 B1* | 8/2009 | Mayor et al. | 356/337 |
| 2004/0036630 A1 | 2/2004 | Jamieson et al. | |
| 2006/0018752 A1 | 1/2006 | LeMieux et al. | |
| 2006/0203242 A1* | 9/2006 | Itoh | G01N 21/9506 356/338 |
| 2007/0133984 A1* | 6/2007 | Maier | G01J 3/28 398/26 |
| 2007/0171396 A1* | 7/2007 | Harris et al. | 356/28 |
| 2009/0128810 A1* | 5/2009 | Bates | G01N 15/1012 356/336 |
| 2009/0323061 A1* | 12/2009 | Novotny | G01N 15/1456 356/336 |
| 2011/0019188 A1 | 1/2011 | Ray et al. | |
| 2011/0149268 A1* | 6/2011 | Marchant et al. | 356/27 |
| 2011/0222048 A1* | 9/2011 | Englert et al. | 356/28.5 |
| 2013/0054187 A1* | 2/2013 | Pochiraju et al. | 702/150 |
| 2013/0293882 A1* | 11/2013 | Dottery | G01J 3/44 356/301 |
| 2014/0016115 A1* | 1/2014 | Shimon | G01S 17/023 356/28 |
| 2015/0055115 A1* | 2/2015 | Pedersen et al. | 356/4.01 |
| 2015/0241461 A1* | 8/2015 | Imaki | G01S 17/95 356/28 |
| 2015/0260846 A1* | 9/2015 | Lyuh | G01S 17/58 250/206.1 |

FOREIGN PATENT DOCUMENTS

| | | |
|---|---|---|
| CN | 101963676 | 2/2011 |
| WO | 2011014712 | 2/2011 |

OTHER PUBLICATIONS

B. Stankov et al: "Remote sensing observations of winter aircraft icing conditions—A case study", Journal of AI RC Raft, vol. 31, No. I, Jan. 1, 1994 (Jan. 1, 1994), pp. 79-89, XP55166501, ISSN: 0021-8669, DOI: 10.2514/3.46458.

Luc R. Bissonnette et al: "Retrieval of cloud liquid water content and effective droplet diameter from multiply scattered lidar returns", Proceedings of SPIE, vol. 4087, Dec. 15, 2000 (Dec. 15, 2000), pp. 939-946, XP55166467, ISSN: 0277-786X, DOI: 10.1117/12.406331.

Alan Derrick et al "Havsnäs Research"; Winterwind, Umeå Feb. 2011.

Test Report 546-01B Operation of the Windcube V2 lidar at CRES Test Station "Lidar verification in complex terrain", Feb. 2011.

\* cited by examiner

ARRANGEMENT AND METHOD FOR ICING DETECTION

FIELD OF THE INVENTION

Generally the present invention pertains to measuring and optics. In particular, the invention is related to icing detection based on optical remote sensing.

BACKGROUND

Contemporary solutions for assessing the icing conditions of various surfaces and related elements differ considerably depending on the implementation and related use scenario.

Atmospheric icing takes place when water droplets in the atmosphere freeze on a contacted object. For example, in connection with aircrafts the ice may increase the risk of stalling of the airfoil. Thereby, the ice built-up should be detected as early and reliably as possible. For instance, an electromechanical probe with an oscillating (vibrating) sensing element may be provided on the nose of the aircraft, whereupon the ice accreted thereon causes changes in the oscillation frequency depending on the thickness of the ice layer. The oscillation frequency is monitored for estimating the amount of ice.

As another use scenario, the wind turbines of wind farms may be heavily affected by ice on the rotor blades. The blades may crack and the production efficiency may drastically decrease. The overall wear of the turbine may also increase due to mass and aerodynamic imbalances and additional friction all caused by the ice. Introduction of the aforesaid oscillating probe into the nacelle of a wind turbine has been suggested, so has been the use of various capacitance-, impedance-, and inductance-based detectors requiring the addition of specific sensors on the rotor blades. Further, different optical sensors monitoring the ice accumulated on a sensor surface based on e.g. changes on light reflection from the surface have been set forth.

However, e.g. the oscillation probe may not suit all use scenarios and may turn out too slow as to the achieved detection response. It is relatively complex by nature and requires integration with the turbine nacelle. The capacitance/impedance/inductance-based sensors may, on the other hand, work unreliably after the first detection as the ice removal from the sensor by heating, for example, may easily at least partially fail, whereupon the subsequent detections may be inaccurate. Similar flaws have been recognized with many optical sensing solutions.

In summary, many known arrangements to detect icing still suffer from reliability problems at least in certain type of operational conditions. Yet, their detection areas are limited as they represent only a single or few points in space, i.e. the sensor surface locations. In any case, the arrangements are merely capable of detecting already-formed ice, which may be too late depending on the application.

To broadly just estimate the icing potential in the atmosphere a number of solutions have been disclosed most of which utilizing a plurality of more or less directly measurable prognostic weather parameters such as temperature and humidity combined via a deduction logic to predict icing. Even these solutions typically bear many weaknesses comparable to the ones already contemplated above.

SUMMARY OF THE INVENTION

The objective is to alleviate one or more problems described hereinabove not yet addressed by the known icing detection arrangements, and to provide a feasible solution for detecting atmospheric icing such as in-cloud icing.

The objective is achieved by the embodiments of an arrangement and a method in accordance with the present invention.

Accordingly, in one aspect of the present invention an arrangement, e.g. one or more devices, for the detection of atmospheric icing conditions comprises a lidar (light detection and ranging) entity, such as a Doppler lidar entity, configured to emit electromagnetic radiation, optionally in a number of directions, to the atmosphere and to receive radiation backscattered from the aerosol, such as a cloud, present in the atmosphere, and a data processing entity configured to obtain at least one indication of signal intensity, such as the CNR (carrier-to-noise ratio) or other indicative parameter, on the basis of the received backscattered signal relative to a number of distances such as heights from a predetermined basic level such as the location of the lidar, further configured to compare the at least one indication of signal intensity with at least one predetermined reference in order to obtain an indication of the likelihood of cloud presence at said number of distances, and configured to determine an indication of the icing potential at said number of distances on the basis of the comparison and an indication of the temperature at said number of distances.

In one embodiment, the lidar includes a Doppler heterodyne (coherent) lidar. The lidar may be a pulsed lidar or a continuous wave lidar. The lidar may utilize wavelengths in the ultraviolet, visible, or near infrared range. Alternatively, an incoherent lidar may be utilized. The lidar may be additionally configured to measure wind speed.

In another embodiment, the data processing entity is configured to obtain a positive indication of the potential presence of a cloud at a distance when the indication of signal intensity, such as a numerical value, substantially corresponds to the reference. Alternatively, a positive indication may be obtained when the indication of signal intensity substantially differs from the reference. In the case of a numerical representation, a substantially larger or smaller value, or a plurality of values in the case of multiple indications or a multi-value indication, may imply such substantial difference mapped to a positive indication of the likelihood of cloud presence. The indication of the likelihood of cloud presence may be of Boolean (0/1) type or more comprehensive indication (e.g. probability) as contemplated in further detail hereinbelow.

In a further embodiment, the arrangement is configured to characterize the icing potential at the number of distances. The characterization may include an indication of a parameter such as the average droplet size and/or liquid water content, for instance.

Still in a further embodiment, the arrangement is configured to determine an indication of precipitation conditions at the number of distances. The indication may be applied in determining the icing potential and/or icing characteristics.

In a further embodiment, the arrangement may be configured to trigger and/or it comprises a countermeasure activation entity configured to trigger anti-icing or de-icing procedure such as a heating or microwave excitation procedure to prevent, reduce or slow down ice accretion on a predetermined surface. The controlled heating or excitation means may be integrated with the arrangement or provided as separate therefrom. Heating may be implemented through blowing hot air or other gas, funneling heated wires or other elements or e.g. heated liquid (by liquid circulation system, for instance) to the target area(s), etc. For anti-icing use the target area(s) may include ice-repellant coating such as silicon paint, for example. Alternatively or additionally, the arrangement may be configured to trigger altering the state of a functionally connected target device such as a wind turbine. The state change may include stopping the turbine or generally, altering the rotation characteristics such as the speed of the rotor, for example.

In a further embodiment, the arrangement is configured, in order to determine the indication of the icing potential, to verify whether the temperature measured and/or estimated fulfills a predetermined condition. For example, in case the temperature is (optionally equal or) below a predetermined threshold or within a predetermined range, e.g. few degrees such as one, two, three or four degrees, relative to a predetermined reference point such as the zero degrees Celsius, i.e. the normal freezing point of water, the arrangement is configured to consider the temperature condition for icing as fulfilled. The range around the reference point may be symmetrically or asymmetrically disposed. The indication of the temperature may thus be of simple Boolean (1/0, True/False) type.

In a further embodiment, the arrangement may be configured to consider the icing as likely when the likelihood of cloud presence is high, e.g. over a predetermined threshold, and the temperature condition for icing is fulfilled as implied by the corresponding indications.

Alternatively, the indication of the temperature used in the determination of the icing potential may be of higher resolution and optionally indicate the measured temperature(s) in full integer or one decimal place centigrade values, for example.

In a further embodiment, the arrangement configured to determine the indication of the signal intensity such as CNR is further configured to compare it with at least one predetermined reference (CNR). The reference may be indicative of substantially clear condition with no clouds. In that case the reference such as the CNR may be low or generally contain small values according to predetermined criterion, for instance, due to the lower amount of backscattered radiation. If the measured indication then substantially differs from the reference, i.e. the measured indication is generally higher according to predetermined criterion or criteria (e.g. predetermined amount of dB), for instance, the likelihood of cloud presence may be deemed high. To the contrary, if the reference indicates cloudy condition, the associated value may be relatively high. As a further alternative depending on the embodiment, the reference may be set to indicate a predetermined threshold scenario somewhere between substantially clear and extremely cloudy conditions, for example.

The likelihood may be indicated via simple 1/0, Yes/No, True/False, or other coarse, substantially Boolean or binary type condition variable, or a more comprehensive numerical range with at least one value between the extremes may be utilized, for example. In such a range, one end may indicate the lowest probability of cloud presence, whereas the opposite end the highest probability.

In a further embodiment, the used reference may be dynamic and/or adaptive. It may be optionally automatically adapted based on at least one factor selected from the group consisting of: time of day, season, month, week, year, time, location, altitude, latitude, longitude, and temperature. Accordingly, the logic for determining the indication of the likelihood of cloud presence and icing potential may be dynamic and/or adaptive.

In some embodiments the actions of comparison and icing potential indication determination may be combined and executed e.g. in parallel. For example, they may result from calculating the same formula(e) utilizing the determined indication of signal intensity and the indication of the temperature as input. In certain embodiments, even the indication determination may be combined therewith. Alternatively, the determination and the comparison actions may be combined.

In a further embodiment, a wind turbine, a windmill or a wind farm comprises at least one aforementioned arrangement of the present invention as separate (system of wind turbine(s) and at least one arrangement) or at least partially integrated therewith. The arrangement may be installed at the turbine hub, rotor, nacelle, tower, base, or it may be disposed on the ground near-by, for instance. Each wind turbine may have a dedicated arrangement, or it may be shared among multiple turbines.

In a further embodiment, the wind turbine, windmill or wind farm may comprise anti-icing and/or de-icing means such as a heating means to prevent the rotor blades and/or other element(s) from icing.

In another aspect of the present invention, a method for detecting atmospheric icing conditions comprises
  emitting, by a lidar entity (light detection and ranging) such as a Doppler lidar entity, electromagnetic radiation, optionally in a number of directions, to the atmosphere and receiving radiation backscattered from the aerosol, such as a cloud, present in the atmosphere,
  determining at least one indication of signal intensity, such as the CNR (carrier-to-noise ratio) or other indicative parameter, on the basis of the received backscattered signal relative to one or more distances such as heights from a predetermined basic level such as the location of the lidar,
  comparing the at least one indication of signal intensity with at least one predetermined reference in order to obtain an indication of the likelihood of cloud presence at said one or more distances, and
  determining an indication of the icing potential at said number of distances on the basis of the comparison and an indication of the temperature at said one or more distances.

The previously presented considerations concerning the various embodiments of the arrangement may be flexibly applied to the embodiments of the method mutatis mutandis and vice versa, as being appreciated by a skilled person.

The utility of the present invention arises from a plurality of issues depending on each particular embodiment. First of all, icing conditions may be predicted and detected preferably prior to the actual icing of the element of interest, such as the blades of the wind turbine, and the proposed icing detection method is reliable. Thus the required counter-procedures such as de-icing procedures or may be started as early as possible and further inconvenience or damage resulting from icing is advantageously overcome. Likewise, control procedures such as turbine control in the context of wind turbines may be enhanced by the knowledge of the prevalent icing conditions. Further, the existing equipment already installed at the destination sites, such as the lidars in conjunction with wind turbines or wind farms, may be applied to implement an embodiment of the present invention, whereupon the necessary additional gear remains moderately modest, which facilitates the adoption phase and reduces the overall cost.

Moreover, the suggested solution also enables estimating the likelihood of icing at several different distances relative to the reference point, which enables situating the arrangement farther away from the actual point of interest. For example, the lidar and optionally the processing entity may be conveniently provided to the nacelle of a wind turbine or even on the ground, while the conditions near the maximum altitude of the blade ends are still monitored.

On the whole, the suggested solution bears potential in various fields where icing has to be monitored and taken into account. For instance, in aviation sector both the ground-based and in-flight uses of the solution are feasible.

The expression "a number of" refers herein to any positive integer starting from one (1), e.g. to one, two, or three.

The expression "a plurality of" refers herein to any positive integer starting from two (2), e.g. to two, three, or four.

The terms "first" and "second" do not denote herein any particular priority or order. Instead, they are used to distinguish one entity such as a physical or logical element from another entity.

The term "aerosol" generally refers herein to a mixture of a gas and solid and/or liquid particles. For example, a cloud may be thus considered as an aerosol.

Different embodiments of the present invention are disclosed in the dependent claims.

BRIEF DESCRIPTION OF THE RELATED DRAWINGS

Next the invention is described in more detail with reference to the appended drawings in which FIG. 1a illustrates a use scenario of an embodiment of the present invention in a wind turbine context.

DETAILED DESCRIPTION OF THE EMBODIMENTS

Lidars applied in connection with various embodiments of the present invention may incorporate laser-based devices capable to remotely measure the property of the atmosphere by sending laser beams in the air and then analyze the signal backscattered from the atmosphere. Lidars designed for wind energy applications can rather often measure the wind speed with high accuracy and precision regarding distances falling within a range from about 10 to about 1000 meters. They may be configured to measure the Doppler shift in the backscattered signal by the moving aerosol and can then possibly reconstruct the wind vector by probing a volume of air with at least three lines of sights. Such devices may allow, for instance, measuring the wind speed at the hub height of modern Multi-MW turbines for energy yield assessment with ground based instruments (staring upwards) but also for turbine control with nacelle mounted devices (staring horizontally). Measurements are not generally limited to only one distance. Wind lidars may focus at one height (continuous wave lidars) at a time or measure the time of the backscattered signal to derive the measurement height (s) (pulsed lidars).

Figure 1A:
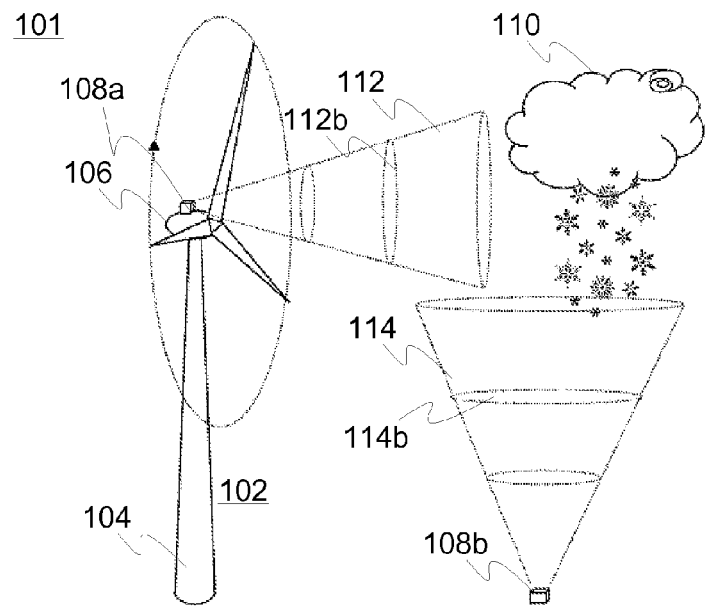
FIG. 1b is a block diagram of an embodiment of the proposed arrangement.

FIG. 1a is a sketch illustrating a use scenario 101 of an embodiment of the arrangement suggested herein. The use scenario 101 incorporates a wind turbine 102 provided with the arrangement. The arrangement includes a lidar 108a, 108b that may be mounted on the nacelle 106 or ground respectively, for instance, such that the cone formed by the emitted beam 112, 114 can be targeted towards predetermined or dynamically adjustable direction scanned by the lidar 108a, 108b. Lidar 108a has been configured so as to scan substantially in the horizontal direction whereas lidar 108b has been positioned on the ground and arranged to scan in the vertical direction. It shall be clear to a skilled person that e.g. the nacelle 106, base, or the tower 104 of the wind turbine 102 may also be provided with a lidar that is configured to emit its beam in a substantially vertical direction or diagonally relative to a reference plane such as the ground. The other entities of the arrangement (not shown in FIG. 1a) may be located in connection with the lidar entity 108a, 108b or be remotely disposed remaining, however, operably connectable therewith.

As mentioned hereinbefore, the lidar 108a, 108b may be a coherent (detection) lidar, such as a coherent Doppler lidar (e.g. pulsed or continuous wave), or an incoherent lidar such as incoherent Doppler lidar. In many use scenarios, a coherent heterodyne Doppler lidar may indeed be applied, for instance.

At least a portion of the electromagnetic energy transmitted by the lidar as a beam of light may be backscattered due to particles such as dust, pollen, or droplets present in the atmosphere and moving at the same velocity as the ambient wind. The velocity of the particles along the measurement beam direction causes a frequency shift in the backscattered signal that may be then applied by a Doppler lidar to estimate the wind speed.

A lidar may be utilized to obtain data about wind speed, turbulence, wind veer and/or wind shear data in addition to being used for estimating the icing conditions in accordance with the present invention. Further, the lidar may be located on a suitable position such as the wind turbine rotor or nacelle to measure oncoming horizontal winds in order to enable adjusting blades to protect components and increase power, for example.

The applied laser may emit wavelength falling within the range of about 600 to 1700 nm, i.e. the wavelength may be about 1500 nm, for instance. A feasible wavelength, cone angle and other measurement parameters, such as pulse width, pulse energy, beam size, focus distance, and/or accumulation time etc., may be selected use scenario—specifically.

For example, Windcube™ lidar (pulsed heterodyne) is an example of a Doppler lidar that may be applicable in connection with the present invention certainly still depending on the particular embodiment and use scenario in question.

Backscattering and related data, i.e. wind parameters and/or icing conditions, may be specifically measured at a predetermined number, i.e. one or more, of heights (or generally distances) 112a, 114b as defined from a reference point such as the lidar equipment itself However, the use of e.g. a pulsed lidar may be preferred so that the backscattering information relative to a plurality of heights may be conveniently obtained without first strictly specifying the measurement heights. A distance to the location of interest (e.g. the location of a wind turbine blade tip in maximum altitude, or the location of the nacelle/hub) may translate as tens or even hundreds of meters, or substantially the immediate vicinity of the lidar entity 108a, 108b, so the range is wide and depends on the embodiment. With somewhat clear sky, backscattering is modest but in cloudy 110 conditions, for example, the signal strength of the backscattered signal is stronger, which may be exploited in determining the icing potential at each height.

Figure 1B:
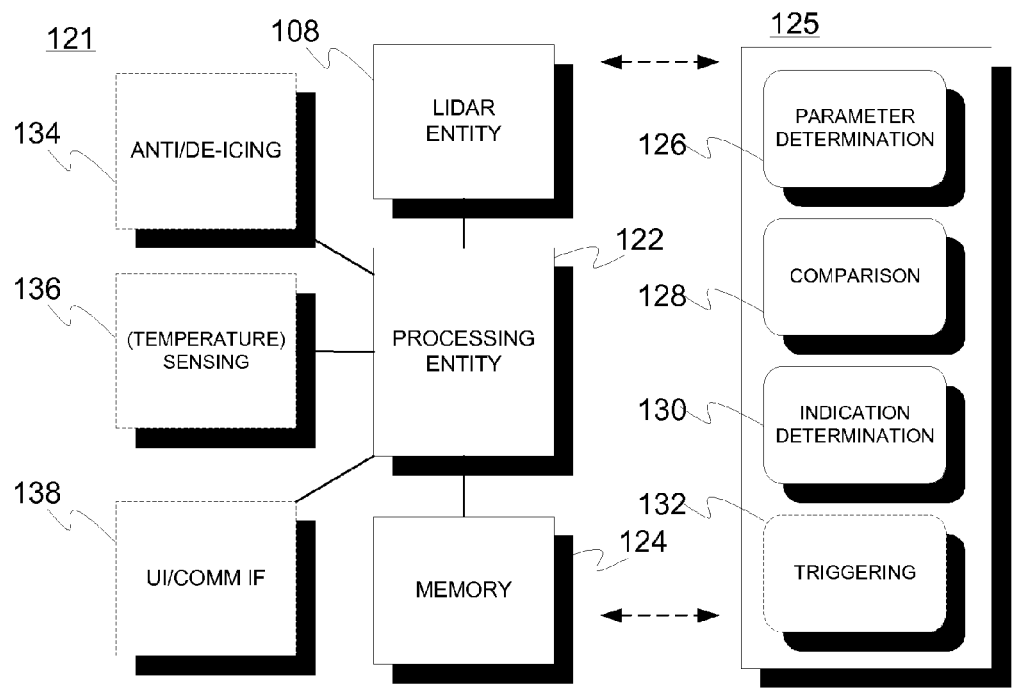

FIG. 1b depicts a block diagram of an embodiment 121 of the proposed arrangement with functional emphasis. Optional features of the embodiment are illustrated with rectangles having a broken outline.

The arrangement 121 is typically provided with one or more processing devices capable of processing instructions and other data, such as one or more microprocessors, micro-controllers, DSPs (digital signal processor), programmable logic chips, etc. The processing entity 122 may thus, as a functional entity, physically comprise a plurality of mutually co-operating processors and/or a number of sub-processors connected to a central processing unit, for instance. The processing entity 122 may be configured to execute the code stored in a memory 124, which may refer to the icing detection software and optionally other software such as counter-measure triggering software in accordance with the present invention. The software may utilize a dedicated or a shared processor for executing the tasks thereof The code may be provided on a carrier medium such as a memory card or an optical disc, or be provided over a communications network.

Similarly, the memory entity 124 may be divided between one or more physical memory chips or other memory elements. The memory 124 may further refer to and include other storage media such as a preferably detachable memory card, a floppy disc, a CD-ROM, or a fixed storage medium such as a hard drive. The memory 124 may be non-volatile, e.g. ROM (Read Only Memory), and/or volatile, e.g. RAM (Random Access Memory), by nature. The memory 124 may also be at least partially integrated with the processing entity 122.

A lidar entity 108 is configured to emit the electromagnetic radiation according to the applied configuration, receive the backscattered signal and provide the measurement data as such and/or in processed format to the processing entity 108 for further use. In some embodiments, the lidar entity 108 may also incorporate at least portion of the processing entity 122 and/or optionally further illustrated and/or other entities.

The UI (user interface) and/or a communications interface entity 138 may comprise a display, e.g. an (O)LED (Organic LED) display, and/or a connector to an external display or a data projector, and a keyboard/keypad or other applicable control input means (e.g. touch screen or voice control input, or separate keys/buttons/knobs/switches) configured to provide the user of the entity with practicable data visualization and/or arrangement control means. The UI may include one or more loudspeakers and associated circuitry such as D/A (digital-to-analogue) converter(s) for sound output, e.g. alert sound output, and a microphone with A/D converter for sound input. The communications interface such as at least one transceiver may incorporate e.g. a radio part including a wireless transceiver, such as WLAN (Wireless Local Area Network), Bluetooth or mobile network (e.g. GSM/UMTS) transceiver for communication with external devices such as sensors 136, monitoring devices, control devices, data capturing devices and/or a network infrastructure, and/or other wireless or wired data connectivity means such as one or more wired interfaces (e.g. LAN such as Ethernet, Firewire, or USB (Universal Serial Bus)) for the similar purpose.

The temperature data utilized in determining the icing potential may be obtained by a number of sensors 136 integrated with or at least operatively connected to the processing entity 122 e.g. via the communications interface 138. Anti- and/or de-icing means 134 may be likewise provided and connected to the processing entity 122.

On the right side of FIG. 1b, as separated by the broken bi-directional arrows from the rest of the arrangement 121, the entity 125 discloses few at least logically noteworthy entities the arrangement 121 preferably includes and/or implements e.g. via combination of measurement data provided by lidar 108, measurement data provided by at least temperature sensor 108, and the software executed by the processing entity 122 and stored in memory 124. Parameter determination block 126 determines an indication of the backscattering signal intensity such as CNR or other signal intensity—indicating parameter based on the backscattered lidar signal for comparison. Received signal strength, or 'level', may in some embodiments be directly used. The procedure may be executed by the lidar 108 itself and/or the processing entity 122. Comparison block 128 refers to comparing the measurement data and/or parameter derived therefrom with reference data to figure out the likelihood of obstacles such as clouds at the measured distances. Indication determination block 130 calculates the indication of the icing potential on the basis of the comparison and further data such as (temperature) sensor data. The temperature data may be associated with own reference data. Triggering entity 132 is configured to trigger a procedure such as de-icing or anti-icing procedures. A triggering signal may be sent towards the procedure-executing entity.

It is clear to a skilled person that the disclosed entity may comprise few or numerous additional functional and/or structural elements for providing beneficial communication, processing or other features, whereupon this disclosure is not to be construed as limiting the presence of the additional elements in any manner.

One or more, e.g. all, constituent entities of the arrangement 121 may be provided in a common housing thus forming a device. Alternatively, the arrangement 121 may be provided as multiple and at least operatively connectable units including at least one physically separable entity selected from the group consisting of: a lidar entity, a main unit (comprising e.g. a processing entity and memory), a sensor such as a temperature sensor, and an anti/de-icing element.

As the backscattered signal intensity typically varies with the different atmospheric conditions, it may be used for data quality check. Data with intensity lower than a predetermined threshold may be treated as bad quality data and be discarded. Backscattered signal intensity is generally higher when there are a lot of particles in the air. For example, small water droplets forming clouds and fog represent a good scattering media for the laser beams of the lidar equipment. Cloudy and foggy conditions in the volume of air probed by the lidar will thus lead to high back scattered signal and signal strength.

Those conditions may lead to icing conditions in an atmosphere with low temperatures. The lidar may be used to detect icing conditions by looking at signal intensity and temperature, for instance.

An embodiment of a procedure to detect icing conditions by measuring the backscattered signal intensity and the temperature of the atmosphere and comparing them with the reference thresholds may be formulated as:

$$\text{if } S(x) > Ts_s(x) \text{ and } T_{air} < Ts_{air} \rightarrow \text{Icing conditions} \quad (1)$$

wherein $Ts_s(x)$ may represent the threshold value for the backscattered signal as a function of distance, $Ts_{air}$ may represent the threshold value for the air temperature, $T_{air}$ may represent the measured or otherwise estimated air temperature (may be distance-specific) and S(x) the intensity of the measured or otherwise estimated backscattered signal. The threshold values for the air temperature may also be distance-specific.

When the criteria are met for a certain distance $x_{ice}$, the icing conditions will be detected and may be optionally further assumed happening at all heights x 22 $x_{ice}$.

Icing conditions intensity at distance x may be considered to be proportional to $S(x)-Ts_s(x)$ and $T_{air}-Ts_{air}$.

Figure 2:
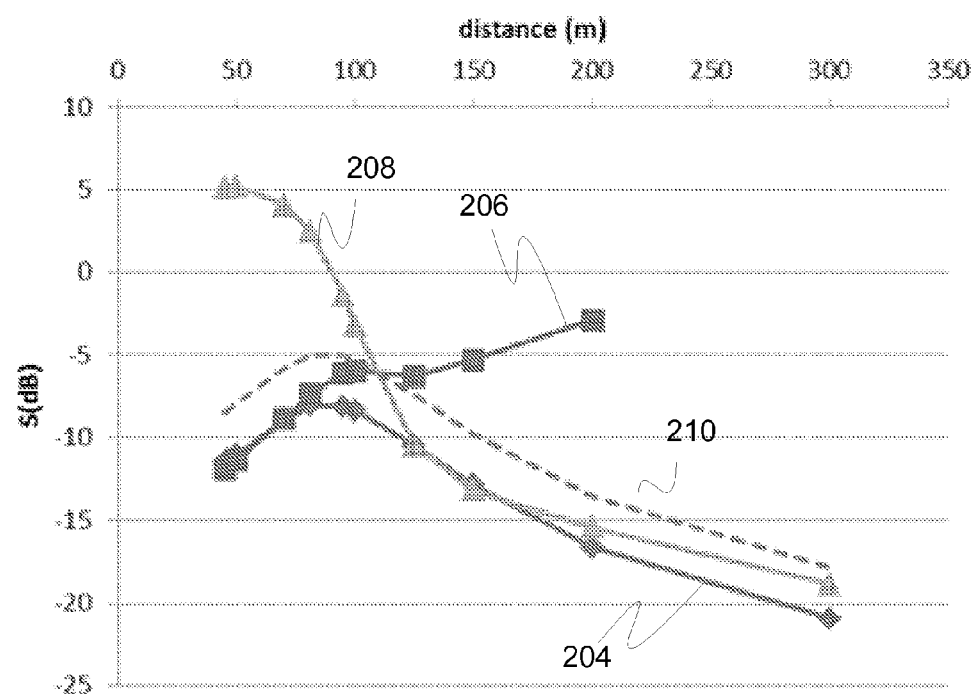
FIG. 2 illustrates examples of measurement data and comparison reference in connection with an embodiment of the suggested solution.

FIG. 2 illustrates, at 201, merely exemplary data (dB) indicative of backscattering signal intensity, such as CNR, in the case of varying conditions on a test site and related reference values (threshold values). The horizontal axis represents altitude (or generally distance) and the vertical axis represents the intensity determined utilizing the backscattered measurement signal captured by the lidar. The shown three curves represent the intensity indications of three different conditions, namely 'no ice' 204, 'ice far' 206, and 'ice near' 208, respectively, whereas the fourth curve 210 indicates the comparison reference (threshold). The indications may have been originally determined for a number of distances and the results may have been then connected resulting in the visualized curves. The indications may have been estimated for the intermediate distances by interpolation, for example, in case no applicable number of true measurements was readily available. E.g. CNR may be considered, as a diagnostic of measurement quality being thus somewhat equivalent to signal to noise ratio, but also applicable in the context of the present invention for evaluating cloudiness.

It is clearly visible in the figure how the shorter distance—relating intensity values of 'ice near' curve 208 and the longer distance—relating intensity values of 'ice far' curve 206 are, by a considerable margin, higher than the distance-wise matching values in the 'no ice' case as indicated by curve 204 or in the reference (threshold) curve 210. The reference 210 may have been theoretically and/or empirically determined to imply conditions that serve as applicable threshold for decision-making. Optionally, a number of selected curve properties (e.g. shape, size, etc.) may be utilized to determine a number of desired parameters or indicators.

The applied thresholds for both intensity and temperature may be tuned site-specifically.

The logic for the method may be implemented via software code that may be further delivered on a carrier medium such as optical disc or memory card, for example. External sensor(s) or lidar-incorporated sensor(s) may be applied for temperature sensing. This kind of a method may be used both for assessment purposes (occurrences of icing conditions) and system control (ice prevention system)

Figure 3:
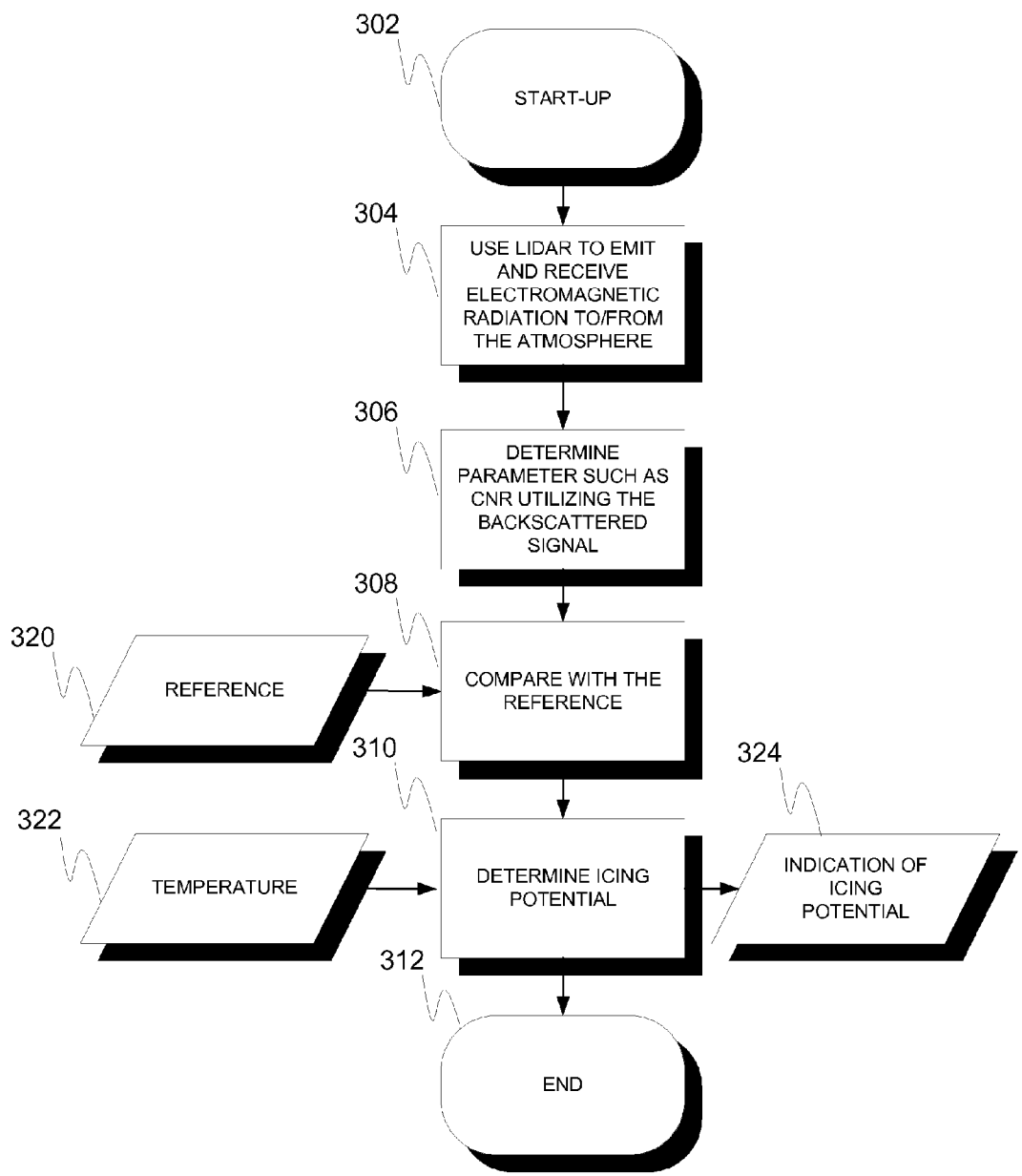
FIG. 3 is a flow chart of an embodiment of the method in accordance with the present invention.

FIG. 3 discloses, by way of example only, a method flow diagram in accordance with an embodiment of the present invention.

At 302, the arrangement for executing the method is obtained and configured, for example, via installation and execution of related hardware and/or software. New hardware and/or software may be installed at the use locations and/or the existing, already available gear such as wind turbine—installed lidar may be configured or tailored according to the principles put forth herein. Execution parameters such as lidar emission and reception parameters (beam wavelength, pulse length, pulse energy, beam diameter, focus points (distances), and/or accumulation time) and/or sensor parameters (e.g. temperature sensor settings) may be set.

At 304, the lidar is applied to emit electromagnetic radiation, i.e. light (visible or non-visible) to the atmosphere and received the backscattered signal therefrom.

At 306, e.g. the backscattered, captured signal may be analyzed to produce at least one indication such as a number of parameters indicative of backscattered signal intensity such as CNR, for instance. The CNR and/or other parameter(s) may be determined for a number of preselected distances (e.g. for the distances having the corresponding reference values available) and the lidar may have been configured accordingly to provide applicable measurement data. Alternatively, a number of distances under interest (e.g. the distances likely associated with backscattering-causing aerosol such as cloud according to the received backscattering signals) may be dynamically determined through the utilization of a pulsed lidar and preferably substantially continuous reference data, for example.

At 308, the at least one indication such as a CNR parameter is compared with a reference 320 that may have been stored in the executing arrangement earlier and is optionally more or less frequently updated, or the reference may be received from an external entity such as a control apparatus.

At 310, the icing potential 324 is determined by utilizing the indication of signal intensity and the reference (i.e. the comparison result), and an indication of the temperature 322. For example, the indication of temperature may be compared with a predetermined temperature reference (threshold).The indication of temperature may be obtained on the basis of truly measuring or at least estimating the temperature at the number of distances, or it may be represent the temperature obtained via some available, however non-optimum, sensor location that still preferably is as near to the locations of interest (at said number of distances) as possible. In some embodiments, only e.g. a wind turbine tower, blade or e.g. nacelle may be provided with a temperature sensor, and the output thereof may be used as such and/or as a source for estimating the temperature at a number of distances through a number of applicable methods such as extrapolation and/or interpolation. An indication of the icing potential may be transmitted to an external entity and/or used to trigger an internal action in the arrangement such as de-icing or anti-icing measure. The indication may be stored in a data log together with optional further data such as temperature and/or parameter such as CNR data, for example.

At 312, the method execution is ended. In many real-life scenarios the execution of various method items may be repeated and even parallel execution thereof is possible. The execution may be substantially continuous. For instance, new measurement data may be gathered by the lidar entity when the processing entity determines the icing potential utilizing the already-obtained data.

The mutual ordering and overall presence of the method items of the method diagrams disclosed above may be altered by a skilled person based on the requirements set by each particular use scenario.

Consequently, a skilled person may, on the basis of this disclosure and general knowledge, apply the provided teachings in order to implement the scope of the present invention as defined by the appended claims in each particular use case with necessary modifications, deletions, and additions, if any.

For example, provided that a lidar for transmitting electromagnetic radiation to the atmosphere and receiving the backscattered portion has already been provided in the target equipment such as a wind turbine, it may be supplemented with at least operatively coupled other necessary elements, such as the data processing entity, data transmission entity and/or sensor(s), for building up an embodiment of the arrangement in accordance with the present invention. In some embodiments, the original lidar equipment may be simply re-reconfigured, i.e. reprogrammed, to also act as the data processing entity, for instance, and even different data interfaces such as transceivers and/or sensor interfaces may be integrated with it.

The invention claimed is:

1. A system for the detection of atmospheric icing conditions comprising:
   a Doppler lidar (light detection and ranging) entity, including a pulsed lidar, configured to emit electromagnetic radiation, in a plurality of directions, to the atmosphere and to receive radiation backscattered from an aerosol, including a cloud, present in the atmosphere, and
   a data processor in electronic communication with the Doppler lidar entity configured to obtain at least one indication of signal intensity including carrier-to-noise ratio (CNR), which is based on the received backscattered radiation relative to at least one altitude of the location of the Doppler lidar entity emitting the electromagnetic radiation, and further configured to compare said at least one indication of the CNR in the signal intensity, with at least one predetermined reference CNR, in order to obtain an indication of the likelihood of cloud presence at said at least one altitude, and configured to determine an indication of the icing potential at said at least one altitude on the basis of the comparison and an indication of the temperature at said at least one altitude.

2. The system of claim 1, wherein the Doppler lidar entity includes Doppler heterodyne lidar.

3. The system of claim 1, further configured to measure wind speed.

4. The system of claim 1, wherein said at least one predetermined reference indicates substantially clear or cloudy conditions.

5. The system of claim 1, further configured to characterize the icing potential optionally by estimating droplet size or liquid water content.

6. The system of claim 1, further configured to determine an indication of precipitation conditions.

7. The system of claim 1, wherein the data processor is further configured to trigger anti-icing or de-icing procedure in response to said indication of the icing potential.

8. The system of claim 1, further comprising an anti-icing or de-icing entity, including at least one of a heating element or a heating system.

9. The system of claim 1, further comprising a temperature sensing entity.

10. The system of claim 1, wherein the data processor is configured to determine the icing potential higher than in a number of other conditions when the at least one indication of signal intensity implies a cloudy condition according to the comparison and the temperature is below a predetermined temperature, optionally particularly when the temperature is within a predetermined range determined by a lower temperature limit and an upper temperature limit.

11. The system of claim 1, configured to adapt the at least one reference on the basis of Doppler lidar entity measurements.

12. A system comprising:
   at least one wind turbine and a system according to claim 1, and,
   a remote monitoring and control station.

13. A wind turbine comprising:
   a system for the detection of atmospheric icing conditions comprising:
      a Doppler lidar (light detection and ranging) entity, including a pulsed lidar, configured to emit electromagnetic radiation, in a plurality of directions, to the atmosphere and to receive radiation backscattered from the aerosol, such as a cloud, present in the atmosphere, and,
      a data processor in electronic communication with the Doppler lidar entity configured to obtain at least one indication of signal intensity including carrier-to-noise ratio (CNR), which is based on the received backscattered radiation relative to at least one altitude of the location of the Doppler lidar entity emitting the electromagnetic radiation, and, further configured to compare said at least one indication of the CNR in the signal intensity, with at least one predetermined reference CNR, in order to obtain an indication of the likelihood of cloud presence at the at least one altitude, and, configured to determine an indication of the icing potential at the at least one altitude on the basis of the comparison and an indication of the temperature at the at least one altitude.

14. A method for detecting atmospheric icing conditions comprising:
   emitting, by a Doppler lidar entity (light detection and ranging), electromagnetic radiation, in a plurality of directions, to the atmosphere and receiving radiation backscattered from the aerosol, such as a cloud, present in the atmosphere, and,
   by a processor:
      a) obtaining at least one indication of signal intensity including carrier-to-noise ratio (CNR), based on: 1) the received backscattered electromagnetic radiation from the Doppler lidar entity; and, 2) based on altitudes of the location of the Doppler lidar entity emitting the electromagnetic radiation,
      b) comparing said at least one indication of the CNR in the signal intensity, with at least one predetermined reference CNR, in order to obtain an indication of the likelihood of cloud presence at each of the altitudes, and,
      c) determining an indication of the icing potential at each of the altitudes on the basis of the comparison and an indication of the temperature at each of the altitudes.

15. The method of claim 14, wherein the icing potential is considered higher than in a number of other conditions when:
   the indication of the likelihood of cloud presence substantially implies cloudy conditions, and,
   the temperature fulfills a predetermined second criterion such as falls within a predetermined range or is below a predetermined threshold.

16. A computer usable non-transitory storage medium having a computer program embodied thereon for causing a suitable programmed system to detect atmospheric conditions, by performing the following steps when such program is executed on the system, the steps comprising:
  a) obtaining at least one indication of signal intensity including carrier-to-noise ratio (CNR), based on backscattered electromagnetic radiation received from a Doppler lidar entity relative to one or more altitudes of the location of the Doppler lidar entity which emitted the electromagnetic radiation which resulted in the backscattered electromagnetic radiation,
  b) comparing said at least one indication of the CNR in the signal intensity with at least one predetermined reference CNR, in order to obtain an indication of the likelihood of cloud presence at said one or more altitudes, and,
  c) determining an indication of the icing potential at said one or more altitudes on the basis of the comparison and an indication of the temperature at said one or more altitudes.

17. The computer usable non-transitory storage medium of claim 16, wherein the steps additionally comprise:
  determining the indication of the icing potential, wherein the icing potential is considered higher than in a number of other conditions when:
    the indication of the likelihood of cloud presence substantially implies cloudy conditions, and,
    the temperature fulfills a predetermined second criterion such as falls within a predetermined range or is below a predetermined threshold.

18. A wind turbine farm comprising:
at least one wind turbine comprising:
  a system for the detection of atmospheric icing conditions comprising:
    a Doppler lidar (light detection and ranging) entity, including a pulsed lidar, configured to emit electromagnetic radiation, in a plurality of directions, to the atmosphere and to receive radiation backscattered from an aerosol, such as a cloud, present in the atmosphere, and,
    a data processor in electronic communication with the Doppler lidar entity configured to obtain at least one indication of signal intensity including carrier-to-noise ratio (CNR), which is based on the received backscattered radiation relative to at least one altitude of the location of the Doppler lidar entity emitting the electromagnetic radiation, and, further configured to compare said at least one indication of the CNR in the signal intensity, with at least one predetermined reference CNR, in order to obtain an indication of the likelihood of cloud presence at the at least one altitude, and, configured to determine an indication of the icing potential at the at least one altitude on the basis of the comparison and an indication of the temperature at the at least one altitude.

* * * * *